United States Patent [19]

Garzia et al.

[11] 4,076,815
[45] Feb. 28, 1978

[54] QUINOXALINE COMPOUND AND COMPOSITION, PROCESS FOR PREPARING COMPOUND, AND METHOD OF COMBATTING CHOLERA THEREWITH

[75] Inventors: Aldo Garzia, Lodi (Milano); William Ferrari, Modena; Andrea Bottazzi, Lodi, all of Italy

[73] Assignee: Istituto Chemioterapico Italiano, S.p.A., Italy

[21] Appl. No.: 771,118

[22] Filed: Feb. 23, 1977

Related U.S. Application Data

[63] Continuation-in-part of Ser. No. 672,123, Mar. 31, 1976, abandoned.

[51] Int. Cl.² .................. A61K 31/505; C07D 403/06
[52] U.S. Cl. ........................... 424/251; 260/250 QN; 542/467
[58] Field of Search .................. 260/240 E, 250 QN; 424/251

[56] References Cited

U.S. PATENT DOCUMENTS

| | | | |
|---|---|---|---|
| 3,671,521 | 6/1972 | Abuel-Haj | 260/250 QN X |
| 3,965,327 | 5/1976 | Cresswell et al. | 260/240 E X |
| 3,969,346 | 7/1976 | Koller et al. | 260/240 E |

OTHER PUBLICATIONS

Chem. Abs. General Subj. Index, vol. 82, 1-6, 1975, pp. 302GS & 303GS.

*Primary Examiner*—Allen B. Curtis
*Attorney, Agent, or Firm*—Bernard & Brown

[57] ABSTRACT

Compositions and a method for combatting cholera using novel substituted quinoxalines represented by the formula

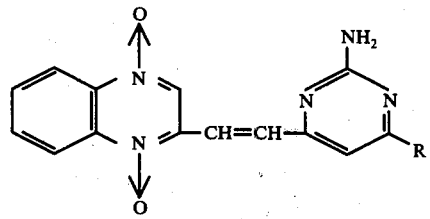

where R is hydrogen or lower alkyl of 1 to 5 carbon atoms, e.g., methyl to pentyl, are provided. A process for preparing the compounds is also provided.

29 Claims, No Drawings

QUINOXALINE COMPOUND AND COMPOSITION, PROCESS FOR PREPARING COMPOUND, AND METHOD OF COMBATTING CHOLERA THEREWITH

This application is a continuation-in-part of application Ser. No. 672,123, filed March 31, 1976, now abandoned.

This invention relates to compounds and compositions useful for, and a method of, combatting cholera. It also relates to a process for preparing the compounds. In a particular aspect, this invention relates to a method of combatting cholera by administration to persons exposed to cholera-producing organisms, a member of a class of substituted quinoxalines, and to a method of combatting cholera by utilizing these quinoxalines to sterilize vibrio organism-containing water.

BACKGROUND OF THE INVENTION

Cholera is a highly infectious disease caused by a vibrio organism. Although the infection can be spread by person-to-person contact, the most common source is contaminated water supplies, the contamination usually arising from sewage containing the organism. Generally, cholera is controlled by administering suitable drugs to the person suffering from the disease. However, there are many advantages to treating exposed persons prophylactically and treating the contaminated water to prevent or greatly reduce the incidence of the disease.

SUMMARY OF THE INVENTION

It is an object of this invention to provide compounds, compositions containing them, and methods using them for combatting cholera.

It is another object of this invention to provide a method of combatting cholera by prophylactic administration of a substituted quinoxaline.

It is a further object of this invention to provide a method of combatting cholera by the prophylactic administration of a substituted quinoxaline which selectively combats the cholera-causing organisms without deleteriously affecting the balance of organisms desired in an environment, e.g., the human biological system, such as, e.g., intestinal flora.

Other objects will be apparent to those skilled in the art from the disclosure herein.

It is the discovery of this invention that substituted quinoxalines (hereafter the "C-Compounds") represented by the formula

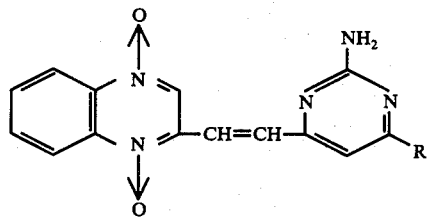

wherein R is hydrogen or lower alkyl of 1 to 5 carbon atoms, e.g., ethyl, propyl, and the like, are useful for combatting cholera-producing organisms. They are especially useful for prophylactic administration prior to development of symptoms of cholera.

DETAILED DISCLOSURE

The C-Compounds of the present invention include but are not limited to
CO-1 2-[2-(2-amino-4-pyrimidinyl)ethenyl]-quinoxaline 1,4-dioxide
CO-2 2-[2-(2-amino-6-methyl-4-pyrimidinyl)ethenyl]-quinoxaline 1,4-dioxide.

These compounds are prepared by reacting, advantageously in an approximately 1:1 mole ratio, quinoxaline-di-N-oxide-2-carboxyaldehyde or its lower alkyl acetals and a compound represented by the formula

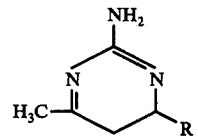

wherein R has the same meaning as defined above.

The reaction is advantageously conducted in the presence of a strong acid catalyst and a suitable solvent, e.g., a lower alkanoic acid such as formic acid or acetic acid. The reaction takes place at reaction temperatures sufficient to effect the reaction and these temperatures can range from ambient, e.g., about 0° C. to elevated temperatures, e.g., 80° C. or more and preferably, e.g., at from about 25° to 50° C. or more. When the reaction is complete, e.g., after about 10 to 24 hours, the product is advantageously recovered by crystallizing it from water.

Catalysts suitable for the practice of this invention are generally known as strong acids and any strong acid known in the art can be used. Suitable strong acids include but are not limited to mineral acids e.g., hydrochloric, hydrobromic, sulfuric, and nitric; aryl sulfonic acids; e.g., toluene sulfonic acid; trichloroacetic acid; etc. The acids are generally used in a ratio of about 0.5-2 moles of acid per mole of quinoxaline starting compound.

The quinoxaline di-N-oxide-2-carboxyaldehyde and its acetals used as a starting material for preparing the compounds of the present invention is known in the art. The acetals can be prepared according to the procedure of Haddadin et al., British Pat. No. 1,305,138, Example XIII, which is incorporated herein by reference thereto. The aldehyde is described in U.S. Pat. No. 3,371,090.

The pyrimidine compounds used as starting materials are similarly known in the art. They are commercially available and the usual commercial grade is suitable. Preferably they should be of good quality, free from deleterious material.

The C-Compounds of the present invention are useful for combatting cholera-causing organisms, e.g., vibrio organisms. The compounds are of a low order of toxicity and are suitable for use by oral administration for prophylactic control of cholera. They are advantageous in that they not only combat cholera-causing organisms, but they can selectively combat the cholera-causing organisms without deleteriously affecting the balance of organisms desired in an environment, e.g., the human biological system.

For oral administration, a C-Compound is usually compounded in a pharmaceutical unit dosage form such as pill, lozenge, tablet or capsule with a pharmaceutically-acceptable carrier. Such unit dosage forms, for example, containing from about 50 to about 500 milligrams of a C-Compound, are quite satisfactory and are prepared according to techniques known to those skilled in the art. Thus, these unit dosage forms will contain the normal diluents, excepients, lubricating agents, and extenders regularly employed in compounding such forms. Exemplary carriers are solids such as lactose and starch and they can be employed in capsules, or tablets in amounts from about 100 to 300 mg. per dosage unit. In general, the administration of a daily dosage of about 1 to 6 capsules or tablets are suitable. The preferred daily dosage is from about 0.3 to 3g per day for about 3 to 5 days.

The compounds are also suitable for use in sterilizing vibrio-organism-containing waters. Typically, above 10, preferably about 10 to about 100 or about 30 to about 100, micrograms per milliliter of water can be used.

The invention will be better understood with reference to the following examples. It is understood, however, that the examples are intended for illustration only and it is not intended that the invention be limited thereby.

EXAMPLE 1

To a reaction vessel there was added 15 ml of 99% formic acid, 1.15 g of 96% sulfuric acid, 1.09 g (0.01 mole) of 2-amino-4-methyl pyrimidine, and 2.36 g (0.01 mole) of quinoxaline -di-N-oxide-2-carboxyaldehyde dimethylacetal. The mixture was heated to 45°–50° and maintained at that temperature for 10 hours. It was then cooled, diluted with 35 ml of cold water and the pH was adjusted to about 5 with sodium bicarbonate. A yellow, crystalline precipitate was formed. It was filtered and washed with water. There was obtained in 64% yield 1.8 g of 2-[2-(2-amino-4-pyrimidinyl)-ethenyl] quinoxaline 1,4-dioxide, m.p. 237-239 with decomposition.

The product, designated CO-1 for convenience, was tested against five strains of vibrio cholerae at concentrations of 10, 30 and 100 micrograms per milliliter. The results are given in Table 1.

Tests were also run to see if the compound was effective against vibrio cholerae El Tor Ogawa 6 in the presence of sewage. Sewage samples were obtained from the sewer system of the city of Modena, Italy. They were centrifuged to separate solids and the supernatant liquid was used in the tests. The results are given in Table 2. At 10 μg/ml of CO-1, there was no growth of 3 of the organisms after 48 hours, and only marginal growth of the remaining two at 100 μg/ml.

Table 1

| | | Effect on Various Strains of *Vibrio Cholerae* | | | | |
|---|---|---|---|---|---|---|
| Compound | Concentration μg/ml | Classical Inaba 35 | Classical Ogawa 41 | El Tor Ogawa 6 | El Tor Ogawa 8 | El Tor Inaba 4 |
| CO-1 | 100 | − | − | ± | − | ± |
| | 30 | − | − | − | − | ++ |
| | 10 | − | − | ++ | − | ++ |
| CO-2 | 100 | − | − | ± | − | ± |
| | 30 | − | − | − | − | ++ |
| | 10 | − | − | ++ | − | ++ |

− No growth after 48 hrs. at 37° C.
± Just noticeable growth
+ Evident growth but to a smaller extent than in untreated control experiments
++ Same degree of growth as in untreated control experiments.

Table 2

| Sample | Concentration of CO-1 | Effect After | | |
|---|---|---|---|---|
| | | 24 hrs. | 48 hrs. | 5 days |
| Control + Vibrion | − | +++ | +++ | +++ |
| Sewage | − | − − − | − − − | − − − |
| Sewage + Vibrion | − | ++3 | +++ | +++ |
| Sewage + Vibrion | 5 γ/ml | − − − | − − − | − − − |
| Sewage + Vibrion | 10 γ/ml | − − − | − − − | − − − |
| Sewage + Vibrion | 20 γ/ml | − − − | − − − | − − − |
| Sewage + Vibrion | 30 γ/ml | − − − | − − − | − − − |

The compound was tested for acute toxicity by several modes of administration in four species, namely, mice, rat, quinea pig, and rabbit. The compound was found to be of a low order of toxicity. The test results are given below in Tables 3, 4, 5 and 6.

Table 3

| | Acute Toxicity of CO-1 in Female Mice | | | |
|---|---|---|---|---|
| Dosage mg/kg | Dead/Treated Animals after | | | |
| | 1 day | 2 days | 4 days | 7 days |
| | Endoperitoneal Administration | | | |
| 2000 | 6/6 | | | 6/6 |
| 1000 | | 6/6 | | 6/6 |
| 500 | | | | 6/12 |
| 250 | | | | 0/18 |
| | Esophageal Administration | | | |
| 0$^{(x)}$ | | | | 0/6 |
| 4000 | | | 1/12 | 1/12 |
| 2000 | | | | 0/12 |
| 1000 | | | | 0/12 |

$^{(x)}$By gastric gavage and receiving only the vehicle.

Table 4

| | | Acute Toxicity of CO-1 in the Rat | | | | |
|---|---|---|---|---|---|---|
| a. | First Experiment | | | | | |
| Sex | Route of Administration | mg/kg | Dead/Treated within 21 days | Body Weight in g. Start | (m±SEM) Termination | Statistical Significance(*) |
| M | Esophageal | 4000 | 0/4 | 234.5 ± 13.8 | 288.7 ± 13.8 | t>0.05 |
| M | Esophageal | 0$^{(x)}$ | 1/4 | 233.7 ± 3.7 | 331.0 ± 0.5 | |
| F | Esophageal | 4000 | 0/4 | 201.2 ± 4.2 | 238.2 ± 12.1 | t>0.05 |
| F | Esophageal | 0$^{(x)}$ | 1/4 | 189.2 ± 3.9 | 230.0 ± 10.5 | |
| M | Endoperitoneal | 500 | 1/4 | 234.0 ± 6.2 | 314.3 ± 10.3 | t>0.05 |
| M | Endoperitoneal | 0$^{(x)}$ | 0/4 | 230.0 ± 5.7 | 324.0 ± 8.7 | |
| F | Endoperitoneal | 500 | 2/4 | 206.2 ± 8.7 | 286.0 ± 272.0 | t>0.05 |
| F | Endoperitoneal | 0$^{(x)}$ | 0/4 | 207.5 ± 4.3 | 253.5 ± 7.7 | |

$^{(x)}$Only the vehicle was administered by the same route.
(*)Student's t test Table 4-continued Acute Toxicity of CO-1 in the Rat b. Second Experiment

| Sex | Route of Administration | mg/kg | Dead/Treated within 7 days | Body Weight in g. Start | (±SE) Termination |
|---|---|---|---|---|---|
| M | Esophageal | 4000 | 0/4 | 222.5 ± 6.2 | 231.7 ± 15.7 |
| F | Esophageal | 4000 | 0/4 | 252.0 ± 16.6 | 253.5 ± 12.1 |
| M | Intraperitoneal | 500 | 2/4 | 226.2 ± 6.8 | 225.0 ± 212 |
| F | Intraperitoneal | 500 | 0/4 | 232.5 ± 5.9 | 218.2 ± 7.0 | c. Cumulative Data Regardless of Animal Sex

| Route of Administration | mg/kg | Dead/Treated within 7 days |
|---|---|---|
| Esophageal | $0^{(x)}$ | 0/8 |
| Esophageal | 4000 | 0/16 |
| Intraperitoneal | $0^{(x)}$ | 0/8 |
| Intraperitoneal | 500 | 4/16 |

$^{(x)}$Only the vehicle was administered.

Table 5

Acute Toxicity of CO-1 in the Guinea Pig By Esophageal Administration

| Dosage, mg/kg | Dead/Treated within 21 days |
|---|---|
| 500 | 0/4 |
| 1000 | 1/4 |
| 2000 | 5/6 |
| 4000 | 6/6 |
| $0^{(x)}$ | |

$^{(x)}$Only the vehicle was administered.

Table 6

Acute Toxicity of CO-1 in the Rabbit By Esophageal Administration

| Dosage, mg/kg | Dead/Treated within 7 days | Body Weight in g. (m±SE) Start | Termination |
|---|---|---|---|
| 2000 | 0/2* | 2250 − 2150 | 2180 − 2140 |
| 1000 | 0/4 | 2037 ± 104.3 | 1922.5 ± 71.5 |
| $0^{(x)}$ | 0/4 | 2135 ± 75 | 2262 ± 215 |
| 500 | 0/2 | 2000 − 2100 | 1650 − 1550 |

$^{(x)}$Only the vehicle was administered.
*There were two dead out of seven treated animals, within 4 days.

In view of the favorable acute toxicity data, the compound was administered orally in sub-acute, but relatively large doses, to mice and rats for 15 days. Data were collected on the effects on death rate, weight, liver and kidneys. The data are given in Tables 7 and 8.

Table 8

Subacute Toxicity of CO-1 in Female Rats
Daily Dose 2 g/kg/day of CO-1 by gastric gavage for 21 days.

| Oral Treatment | Dead/ Treated | Body Weight in g (m ± SE) Start | Termination |
|---|---|---|---|
| Vehicle | $2/6^{(x)}$ | 200.0 ± 4.1 | 233.2 ± 5.1 |
| CO-1, Oral | $1/6^{(x)}$ | 204.1 ± 2.0 | 210.6 ± 9.6 |

| Treatment | Average Percent Weight of Fresh Organs (m ± SE) | | |
|---|---|---|---|
| | Lung | Liver | Kidneys |
| Vehicle (3 animals) | 0.85 ± 0.06 | 3.45 ± 0.07 | 0.95 ± 0.04 |
| CO-1 (5 animals) | 1.07 ± 0.09 NS | 4.54 + 0.10 $HS^{(x)}$ | 1.04 ± 03 NS |

$^{(x)}$Death caused by a mistake in esophagus incannalutation. This diagnosis was confirmed at the post-mortem examination.

In view of the favorable sub-acute toxicity, the chronic toxicity in female mice was studied. The results are given in Table 9.

Table 7

Subacute Toxicity of CO-1 in the Mouse
Daily Dose: 500 mg. CO-1 by gastric gavage for 15 days.

| Oral Treatment | Dead/Treated | % Body Weight Change (m±SE) | Fresh Organ-to-Body Weight Ratio | |
|---|---|---|---|---|
| | | | Liver | Kidneys |
| Vehicle | 0/10 | 20.4 ± 4.2 | 5.2 ± 0.2 | 1.4 ± 0.1 |
| CO-1, 500 mg/kg/day | 0/10 | −8.1 ± 3.9 | 5.9 ± 0.3 | 1.5 ± 0.1 | a. Mortality and Body Weight
Daily Dose: 1 g/kg/day for 15 days.

| Oral Treatment | Dead/Treated | % Body Weight Change |
|---|---|---|
| Vehicle (H$_2$O) | 0/12 | 24.54 ± 0.64 |
| CO-1 in H$_2$O, 1 g/kg/day | 2/12 | 18.5 ± 0.75 |
| Vehicle (adraganth gum) (x) | 0/12 | 25.04 ± 1.18 |
| CO-1 in adraganth gum | 3/12 | 16.27 ± 1.31 | b. SGOT and SGPT (24 hrs. after last dose.)

| Oral Treatment | Units/ml | |
|---|---|---|
| | SGOT | SGPT |
| Vehicle: | | |
| Water | 116 | 4 |
| Adraganth gum | 119 | 6 |
| CO-1 in water | 124 | 9 |
| CO-1 in adraganth gum | 132 | 10 |

Table 9

Chronic Toxicity in the Female Mouse Daily treatment by gastric gavage for 18 weeks (4.5 months)

Table 9

Chronic Toxicity in the Female Mouse Daily treatment by gastric gavage for 18 weeks (4.5 months)

a. Mortality and Body Weight

| Oral Treatment | Dead/ Treated | Body Weight Start | in g (m ± SE) Termination |
|---|---|---|---|
| Vehicle | 3/10 | 28.2 ± 1 | 33.0 ± 1.1 |
| CO-1, 500 mg/kg/day | 2/10 | 30.4 ± 0.9 | 30.0 ± 0.7 |
| CO-1, 250 mg/kg/day | 0/10 | 27.3 ± 0.5 | 26.7 ± 0.7 | b. Urine excretion. Urine amount excreted by 6 animals in 6 hours

| Oral Treatment | Urine Amount (ml) |
|---|---|
| Controls | 6 |
| CO-1, 500 mg/kg/day | 7 |
| CO-1, 250 mg/kg/day | 6.5 | c. Blood glucose. Mean values for 6 animals. Blood samples were taken 24 hours after the last dose

| Oral Treatment | Blood Glucose |
|---|---|
| Controls | 1.14 |
| CO-1, 500 mg/kg/day | 1.06 |
| CO-1, 250 mg/kg/day | 1.10 | d. SGPT and SGOT. Mean values for 6 animals. Blood samples were taken 24 hours after the last dose

| Oral Treatment | Units/ml SGOT | SGPT |
|---|---|---|
| Controls | 125 | 5 |
| CO-1, 500 mg/kg/day | 159 | 6 |
| CO-1, 250 mg/kg/day | 118 | 5 | e. Fresh Weights of Organs

| Oral Treatment | Fresh Organ-to-Body Weight Ratio (m ± SE, 4 animals) | | | |
|---|---|---|---|---|
| | Kidneys | Heart | Liver | Lungs |
| Controls | 0.938 ± 0.044 | 0.481 ± 0.055 | 4.57 ± 0.15 | 0.674 ± 0.044 |
| CO-1, 500 mg/kg/day | 1.07 ± 0.04 | 0.47 ± 0.02 | 4.66 ± 0.91 | 1.011 ± 0.110 |
| CO-1, 250 mg/kg/day | 0.87 ± 0.08 | 0.60 ± 0.08 | 4.57 ± 0.25 | 0.731 ± 0.035 |

In view of the favorable results on chronic toxicity, a teratogenetic study was conducted with male and female mice and rats. The number of young delivered live at birth was comparable with controls. No malformations in either group were observed. The data are given in Table 10.

Table 10

Teratogenetic Study a. Animal Species: Mouse. Male and female mice housed together for 10 days. Oral treatment from 3rd day to 13th days

| Oral Treatment | Pregnant /Treated Animals | No. of Living Fetuses per Delivery (m ± SE) | Body Weight of Fetuses in g (m ± SE) | No. of Fetuses with Malformations |
|---|---|---|---|---|
| CO-1, 250 mg/kg/day | 3/10(x) | 10.3 ± 0.6 | 1.42 ± 0.05 | 0 |
| Controls | 9/10 | 9.0 ± 0.9 | 1.46 ± 0.07 | 0 |

(x)On the basis of our wide experience, the above result might be casual. The study should be repeated to determine whether CO-1 actually prevents pregnancy.

b. Animal Species: Rat. Same experimental conditions as with the mouse.

| Oral Treatment | Pregnant /Treated Animals | No. of Living Fetuses per Delivery (m ± SE) | Body Weight of Fetuses in g (m ± SE) | No. of Fetuses with Malformations |
|---|---|---|---|---|
| CO-1, 250 mg/kg/day | 7/10 | 10.8 ± 0.86 | 7.08 ± 0.19 | 0 |
| Controls | 6/10 | 11.3 ± 1.12 | 6.82 ± 0.40 | 0 |

Compound CO-1 is administered to humans exposed to cholera under epidemic conditions in dosages of from 0.3 to 5 g per person per day for 3–5 days. None of the treated persons become infected but numerous ones with whom they are in daily contact do become infected. It is determined that CO-1 is effective by oral administration as a prophylactic agent in preventing cholera. The CO-1 is also advantageous in that it selectively combats, e.g., inhibits growth of cholera-causing microorganisms, cholera without deleteriously affecting the organisms in the human biological system.

EXAMPLE 2

To a reaction vessel there was delivered a solution of 1.15 g of 96% sulfuric acid dissolved in 25 ml acetic acid, 1.23 g (0.01 mole) of 2-amino-4,6-dimethyl pyrimidine and 1.9 g (0.01 mole) of 2-formyl-quinoxaline-di-N-oxide. The mixture was heated at 40° C. for 16 hours, then cooled, diluted with water and adjusted to pH 5 with sodium bicarbonate solution. The resulting yellow, crystalline precipitate was filtered and washed to give, in 71% yield, 2.1 g of 2-[2-(2-amino-6-methyl-4-pyrimidinyl)-ethenyl]-quinoxaline 1,4-dioxide, designated as CO-2 for convenience. It melted with decomposition at 240° C.

The product was tested against the five strains of vibrio cholerae as described in Example 1. The results are given in Table 1. There was no growth after 48 hours of 3 of the organisms at 10 g/ml of CO-2 and only marginal growth of the remaining two at 100 g/ml.

Compound CO-2 is tested for toxicity in the same manner as described for CO-1 in Example 1. Comparable results are obtained showing that the compound is suitable for prophylaxis.

Compound CO-2 is administered to humans exposed to cholera under epidemic conditions in dosages of from 0.3 to 5 g per day for 3 to 5 days. None of the treated persons become infected but numerous ones with whom they are in daily contact do become infected. It is determined that CO-2 is effective by oral administration as a prophylactic agent in preventing cholera.

Compounds containing, respectively, 6-ethyl, propyl, butyl and pentyl substituents instead of the 6-methyl substitutent can be similarly used as a prophylactic agent.

We claim:

1. A composition comprising an effective amount of a substituted quinoxaline represented by the formula

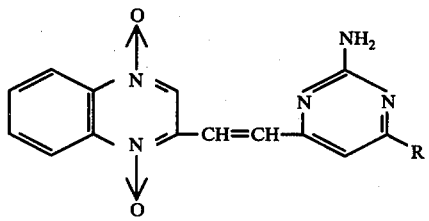

where R is hydrogen or lower alkyl of 1 to 5 carbon atoms, and a pharmaceutically acceptable carrier.

2. The composition of claim 1 in suitable form for oral administration and where R is hydrogen.

3. The composition of claim 1 in suitable form for oral administration and where R is methyl.

4. A method of combatting the growth of cholera-producing organism in water by incorporating in the water an effective amount of a substituted quinoxaline represented by the formula

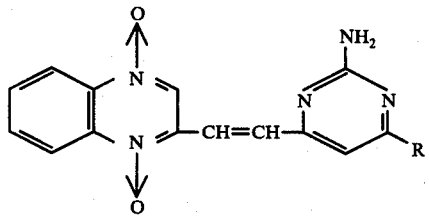

where R is hydrogen or lower alkyl of 1 to 5 carbon atoms.

5. The method of claim 4 wherein the cholera-producing organism is a vibrio organism.

6. The method of claim 5 wherein the amount of quinoxaline incorporated in water is from about 10 to about 100 µg/ml.

7. The method of claim 5 wherein the vibrio organism is a vibrio cholerae organism.

8. The method of claim 7 wherein R is hydrogen.

9. The method of claim 7 wherein R is methyl.

10. A method of claim 7 wherein the amount of quinoxaline compound incorporated in water is from about 30 to about 100 µg/ml.

11. A method of combatting cholera by administration to an individual exposed to a cholera-producing organism an effective amount of a substituted quinoxaline represented by the formula

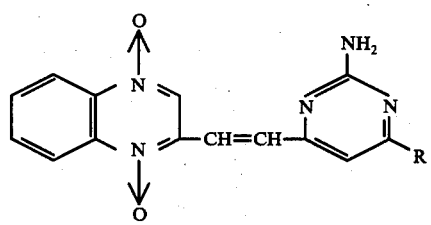

wherein R is hydrogen or lower alkyl of 1 to 5 carbon atoms.

12. The method of claim 11 wherein the cholera-producing organism is a vibrio organism and the quinoxaline is prophylactically administered.

13. The method of claim 12 wherein the vibrio organism is a vibrio cholerae organism and the quinoxaline is orally administered.

14. The method of claim 13 wherein R is hydrogen.

15. The method of claim 13 wherein R is methyl.

16. The method of claim 14 wherein the prophylactic administration includes the administration of from about 0.3 to 5 g per day of the quinoxaline compound to a human exposed to the vibrio cholerae organism.

17. The method of claim 16 wherein the prophylactic administration is conducted for about 3 to 5 days.

18. The method of claim 15 wherein the prophylactic administration includes the administration of about 0.3 to 5 g per day of the quinoxaline compound to a human exposed to the vibrio cholerae organism.

19. The method of claim 18 wherein the prophylactic administration is conducted for about 3 to 5 days.

20. A quinoxaline compound represented by the formula

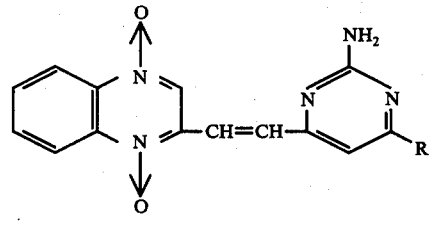

where R is hydrogen or lower alkyl of 1 to 5 carbon atoms.

21. The compound of claim 1 where R is hydrogen.

22. The compound of claim 1 where R is methyl.

23. A process for preparing quinoxaline compounds which comprises reacting a quinoxaline -di-N-oxide-2-carboxyaldehyde dimethylacetal and a compound represented by the formula

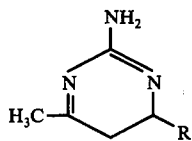

wherein R is hydrogen or lower alkyl of 1 to 5 carbon atoms, under reaction conditions sufficient to produce a quinoxaline compound represented by the formula

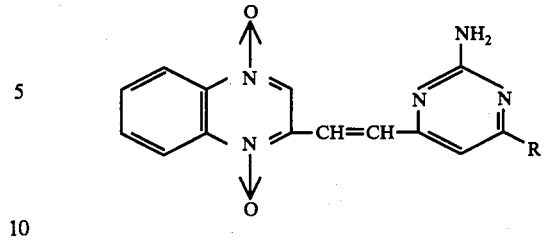

where R has the same meaning as defined above.

24. The process of claim 23 wherein the reaction is catalyzed and is conducted at temperatures from about 0° C. to 80° C. in a solvent.

25. The process of claim 24 wherein the reactants are reacted in an approximately 1:1 mole ratio and the catalyst is a strong mineral acid.

26. The process of claim 25 wherein the solvent is a lower alkanoic acid.

27. The process of claim 23 wherein R is hydrogen.

28. The process of claim 23 wherein R is methyl.

29. The process of claim 26 wherein R is hydrogen or methyl.

* * * * *